United States Patent [19]

Heaven

[11] Patent Number: 5,722,931

[45] Date of Patent: Mar. 3, 1998

[54] FEMALE INCONTINENCE DEVICE

[75] Inventor: Malcolm D. Heaven, Hopewell, N.J.

[73] Assignee: Urohealth Systems, Inc., Costa Mesa, Calif.

[21] Appl. No.: 610,866

[22] Filed: Mar. 5, 1996

[51] Int. Cl.[6] ....................................................... A61F 2/00
[52] U.S. Cl. ........................... 660/29; 600/30; 600/31; 604/327; 604/328
[58] Field of Search ........................ 600/29–31; 604/317, 604/327, 328, 329, 330, 368; 128/885, 834, 836, DIG. 25; 623/12

[56] References Cited

U.S. PATENT DOCUMENTS

| | | | |
|---|---|---|---|
| 4,172,066 | 10/1979 | Zweigle et al. | 604/368 |
| 5,090,424 | 2/1992 | Simon et al. | |
| 5,148,825 | 9/1992 | Gil et al. | 137/78.3 |
| 5,352,182 | 10/1994 | Kalb et al. | |
| 5,360,402 | 11/1994 | Conway et al. | |
| 5,476,434 | 12/1995 | Kalb et al. | 600/30 |
| 5,509,427 | 4/1996 | Simon et al. | 600/29 |
| 5,520,672 | 5/1996 | Urry | 604/368 |

FOREIGN PATENT DOCUMENTS

WO 94/26215   11/1994   WIPO.

*Primary Examiner*—Jennifer Bahr
*Assistant Examiner*—Rosiland Kearney
*Attorney, Agent, or Firm*—Burns, Doane, Swecker & Mathis, L.L.P.

[57] ABSTRACT

A female incontinence device according to the present invention includes one or more rings of water swellable gel forming material mounted on a female incontinence plug or catheter. The water swellable ring swells upon insertion of the device into the urethra and non-traumatically secures the device in the urethra while providing a seal between the device and the walls of the urethra. The water swellable ring may be replaced by other stimuli sensitive materials which allow the ring to be swollen and later reduced in volume for removal of the device. The stimuli sensitive materials which may be used in the invention include materials sensitive to light, pH, electrical field, mechanical stress, temperature, and solvent interaction.

23 Claims, 3 Drawing Sheets

FEMALE INCONTINENCE DEVICE

FIELD OF THE INVENTION

The present invention relates to an improved device for controlling leakage of urine in an incontinent female, and more particularly, to valved catheters and plugs for use in controlling female incontinence.

DESCRIPTION OF THE RELATED ART

The urinary tract system aids the body in ridding itself of waste. The kidneys process blood at a high rate and filter waste products from the circulatory system, creating urine to remove the waste. The ureters drain urine from the kidneys into the bladder, which serves as a reservoir until urination. The bladder has a storage capacity which ranges from approximately one-quarter to one-half liter. The urinary sphincter is a muscle at the base of the bladder which surrounds the bladder neck and urethra and aids the bladder in maintaining continence. The urethra is the tube through which urine flows when the bladder empties.

In the urinary tract, continence, or appropriate storage of urine, is maintained by a complex interplay of anatomic structures. In a normal system, the bladder neck and the urinary sphincter work in a coordinated fashion to act as a valve. During urination, the urethra and urinary sphincter muscles relax and open, the bladder contracts and the bladder neck opens, all in a coordinated fashion, causing the passage of urine. When the bladder neck opens involuntarily in response to intra-abdominal pressure, the lower portion of the urinary sphincter tightens in turn to maintain continence. Similarly, the urethra is also under muscular control to keep this tube closed during the urine storage phase.

A malfunction in any part of this system can cause urinary incontinence (UI) or loss of urine. The most common anatomic incontinence pathology is bladder neck or urethra hypermobility, which results from a lack of bladder neck support caused primarily by weak surrounding tissue. The weakening of tissue surrounding the bladder, urethra and bladder neck arises most commonly in women as a consequence of pelvic trauma caused by pregnancy and childbirth. Other causes of incontinence include physiological, anatomical and neurological disorders.

According to the U.S. Department of Heath and Human Services, there are approximately 10 million UI sufferers in the United States, of which it is estimated that approximately 85% am women. The total worldwide population suffering with UI for developed countries is approximately 22 million women. UI afflicts women of all ages, primarily those over 40, and tends to get worse over time. Women have short urethras and hence less occlusive force. More importantly, women suffer significant pelvic trauma during pregnancy and childbirth. In pregnancy and childbirth, a woman's pelvic nerves and muscles are stretched to a great degree and, as a result, the continence function is often impaired. Therefore, UI shows an increase in incidence as a function of the number of children born to a woman.

Devices such as urinary plugs and catheters are used to prevent urine leakage in incontinent females. Urinary plugs generally are disposable devices. An example of such a device includes a shaft with one or two integral balls thereon. When inserted in the urethra the ball(s) occludes the urethra and holds the device in place until such time as the patient wishes to void, whereupon the plug is physically removed in order to allow urine to flow. Such a device is manufactured by PharmaPlast of Denmark. Another plug type device, manufactured by Uromed Corporation, uses an inflated balloon to retain the device in place. This type of device is disclosed in U.S. Pat. No. 5,090,424 to Simon et al. and in WO94/26215 to McLaughlin et al. Another similar plug type device is manufactured by Rochester Medical Corporation, and is disclosed in U.S. Pat. No. 5,360,402 to Conway et al.

Another device for preventing urine leakage is a valved catheter, which is left in the urethra for a period of time, typically for one month. During this time, voiding is accomplished by inserting a tube into the valve to allow urine to flow. Such a device is disclosed in U.S. Pat. No. 5,352,182 to Kalb et al.

Several problems are associated with the above described devices. Due to irritation of the bladder neck, it is not unusual for a bladder spasm to occur, which can expel the device. The devices are frequently somewhat traumatic, and erosion of the bladder neck is possible. Additionally, given the variety of shapes and sizes of the female urethra, a wide range of sizes of these devices may be needed in order to accommodate urethra of different lengths and diameters. This can lead to problems in correct device sizing, and inventory problems in manufacturing. Accordingly, there is a need in the art for a device which addresses these problems.

SUMMARY OF THE INVENTION

The device according to the present invention addresses the disadvantages of the prior art incontinence devices. The invention offers improved performance over known incontinence devices and accommodates different urethra sizes with reduced trauma to the bladder neck.

According to one aspect of the present invention a female incontinence device includes a body having an enlarged retention head at a first end, a removal portion or meatal anchor at a second end, and a water swellable ring of a gel forming material disposed about the body for securing the body within a female urethra and for preventing leakage between the body and the walls of the urethra. The ring may be of a stimuli sensitive hydrophilic polymer which changes size in response to a stimuli.

According to another aspect of the present invention a female incontinence device includes a tubular catheter body having an enlarged retention head at a first end thereof, a valve which prevents fluid from passing through the tubular catheter body, and a water swellable ring disposed about the tubular catheter body for securing and sealing the catheter body within a female urethra.

BRIEF DESCRIPTION OF THE DRAWINGS

The invention will be described in greater detail with reference to the accompanying drawings in which like elements bear like reference numerals, and wherein.

DETAILED DESCRIPTION OF THE PREFERRED EMBODIMENTS

The present invention offers a way to improve the performance of the types of known valved catheter and plug devices described above. The invention utilizes one or more swellable ring sections mounted on a plug or catheter. The ring sections swell upon insertion to non-traumatically secure the device in the urethra.

Figure 1A:
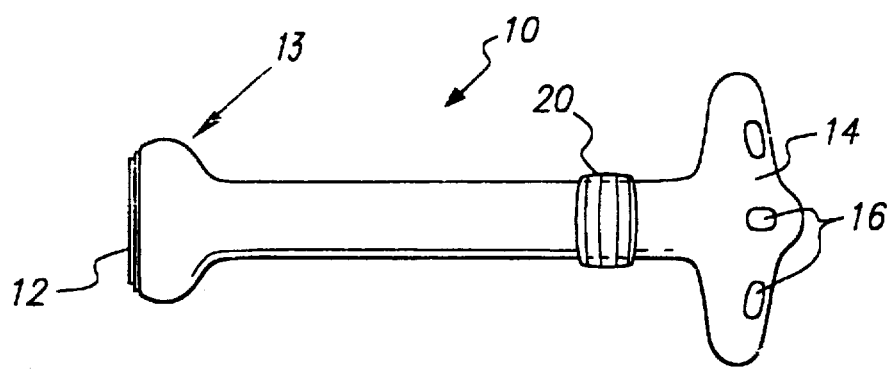
FIG. 1a is a side view of a valved catheter for female urinary incontinence according to a first embodiment of the present invention, with a swellable portion in an unswollen state.
Figure 1B:
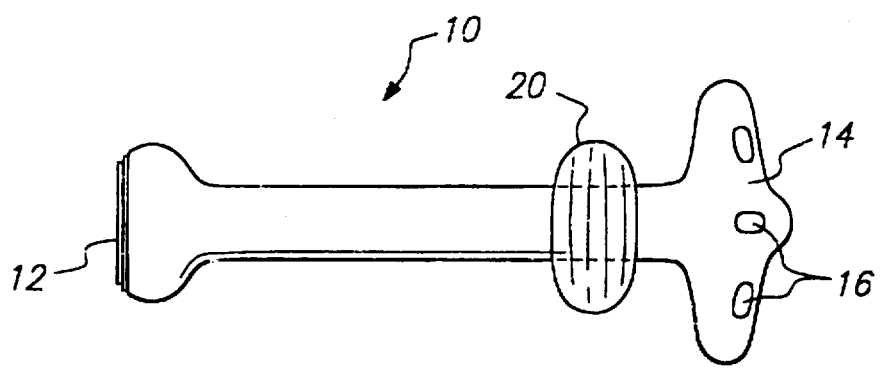
FIG. 1b is a side view of the catheter of FIG. 1a with the swellable portion in a swollen state.
Figure 2:
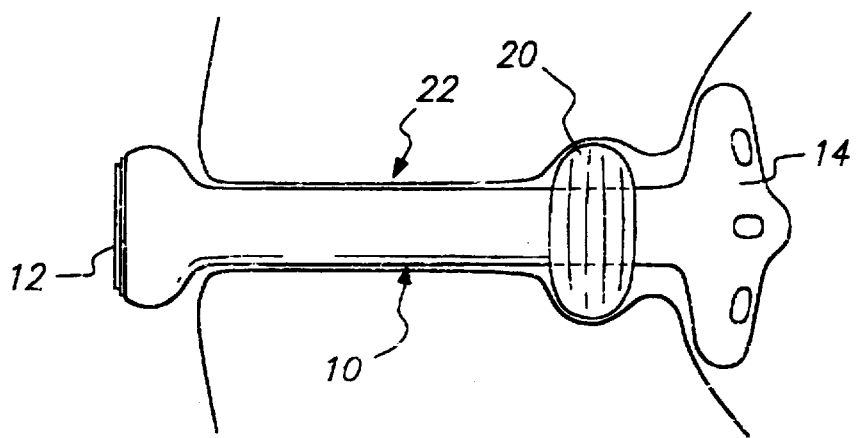
FIG. 2 is a side sectional view of the catheter according to FIGS. 1a and 1b, positioned within a urethra.

According to the embodiment of the device shown in FIGS. 1a, 1b, and 2, a valved catheter body 10 includes a narrow band 20 of water swellable hydrophilic polymer which forms a gel when contacted with water. For instance, the polymer can be a hydrophilic aliphatic polyurethane. A suitable water swellable hydrophilic polymer is manufactured by Kingston Technologies of Dayton, N.J. and sold under the name "HYPAN HYDROGEL". The band 20 shown in FIG. 1a is a thin ring in the unswollen state and, as shown in FIG. 1b, the band 20 is generally donut shaped in the swollen condition with rounded atraumatic edges.

The catheter 10 of FIG. 1a includes a one-way valve 12, such as a duck-bill valve, at one end thereof, a removal or meatal anchor 13, and an enlarged retention head 14 at an opposite end. Although the valve 12 is shown as located at an end of the catheter, it may be positioned at other locations within the catheter. The retention head 14 includes apertures 16 which allow urine to flow into the interior of the catheter. The retention head 14 is preferably of the type which may be elongated for insertion by passing a rigid member through the valve 12 and up though the catheter body 10 to elongate the retention head along the axis of the catheter. This elongation reduces the diameter of the retention head 14 for insertion or removal.

In operation, the catheter 10 is inserted into the urethra with the band 20 of water swellable material in the unswollen state. Upon exposure to urine, the hydrophilic material forms a gel in the swollen state, as shown in FIG. 2. The swollen band 20 takes up any free space that may exist between the catheter body 10 and the urethra 22, and gently forms a seal which prevents leakage between the exterior of the catheter and the urethra. Due to the soft, yielding nature of the gel, the catheter body 10 can be gently withdrawn without any trauma to the urethra 22. Due to the tendency for the urethra to relax locally over time it is advantageous to the patient to alternate the position of the swellable band 20 from one use to the next, thus minimizing the length of time any particular portion of the urethra is dilated.

Figure 3A:
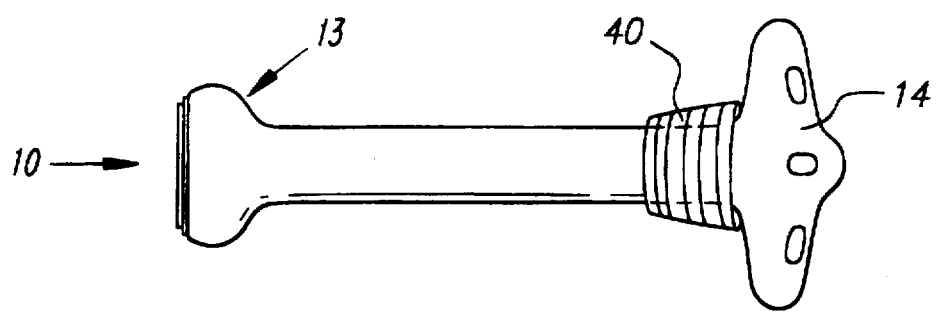
FIG. 3a is a side view of a valved catheter for female urinary incontinence according to a second embodiment of the present invention, with the swellable portion in an unswollen state.
Figure 3B:
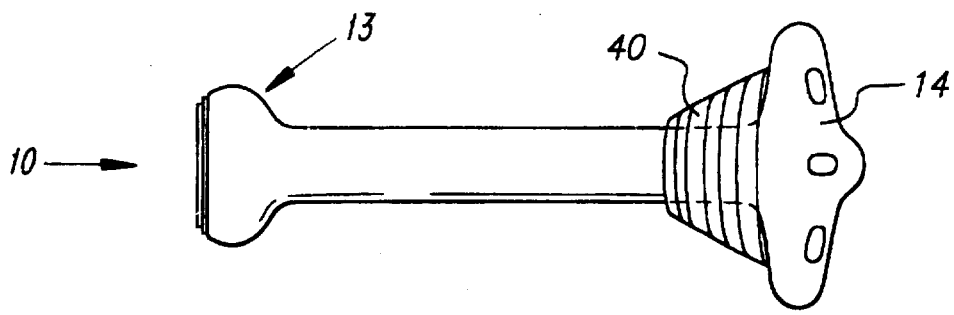
FIG. 3b is a side view of the catheter of FIG. 2a with the swellable portion in a swollen state.
Figure 4:
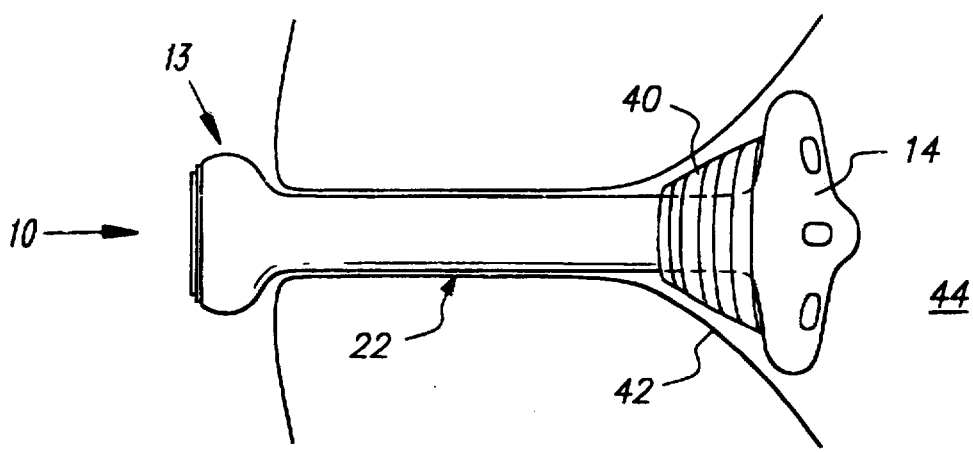
FIG. 4 is a side sectional view of the catheter according to FIGS. 3a and 3b, positioned within a urethra.

Another embodiment of the present invention, illustrated in FIGS. 3a, 3b, and 4, includes a conical ring increasing in diameter in a direction away from a first end 41. The ring 40 is of hydrophilic material 40 surrounding the valved catheter body 10. The ring 40 is designed to fit in the region of the bladder neck 42 typically immediately beneath the retention head 14 of the catheter. Upon swelling, the conical ring 40 of this embodiment tends to exert a gentle force on the bladder neck 42 tending to maintain the retention head 14 of the catheter body 10 in the bladder 44. The ring 40 thus aids in overcoming the tendency of the bladder neck to expel the device from the urethra 22.

A catheter body including a combination of a first section with a band 20 and a second section with a conical ring 40 may optimize results somewhat by providing the benefits of each of these swellable sections.

Figure 5:
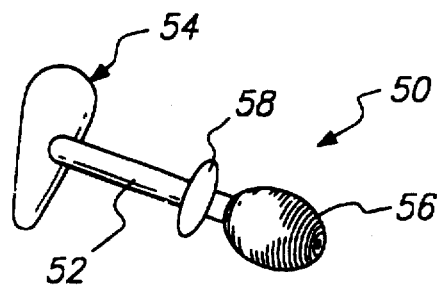
FIG. 5 is a perspective view of a urethral plug according to the present invention.

According to a third embodiment of the present invention, as illustrated in FIG. 5, a plug type device 50 includes a shaft 52, a plate 54 forming a removal meatal anchor, and a solid ball, hollow ball or inflatable retention head 56. The plug 50 incorporates at least one hydrophilic ring 58 in the shape of either a band 58 as shown or a cone (not shown). The hydrophilic ring 58 helps to seal and retain the plug in the urethra. According to the embodiment of FIG. 5, the plug 50 having the swellable band 58 is completely removed from the urethra when the patient wishes to void. The retention head 56 of the plug 50 may also be made of a hydrophilic material.

In most instances the configurations described above are designed such that the catheters and plugs can be withdrawn without difficulty with the swellable bands 20 or conical rings 40 in the swollen state. However, there may be instances where, due to the need for a particularly large occluding section, it would be convenient to reverse the swelling of the material to facilitate easier removal. In this instance, the material used for the band or cone can be based on a stimuli sensitive polymer. Known stimuli sensitive polymers include those which undergo a phase change which substantially alters the swelling characteristics of the material in response to a stimuli. Suitable stimuli include pH change, electrical field, mechanical stress, temperature, solvent interaction, light or combinations thereof.

Figure 6A:
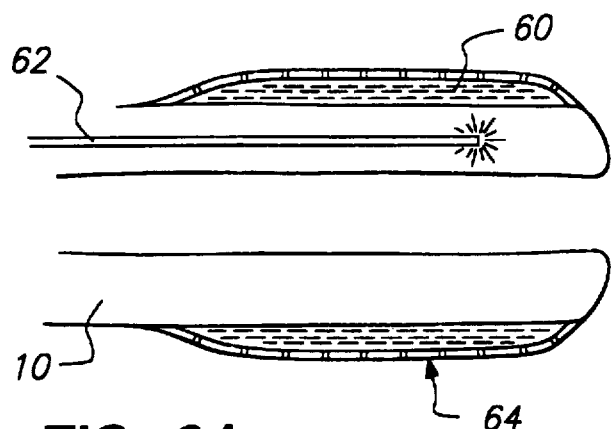
FIG. 6a is a side sectional view of a portion of a valved catheter for female urinary incontinence according to a third embodiment of the invention, with the swellable portion in an unswollen state.
Figure 6B:
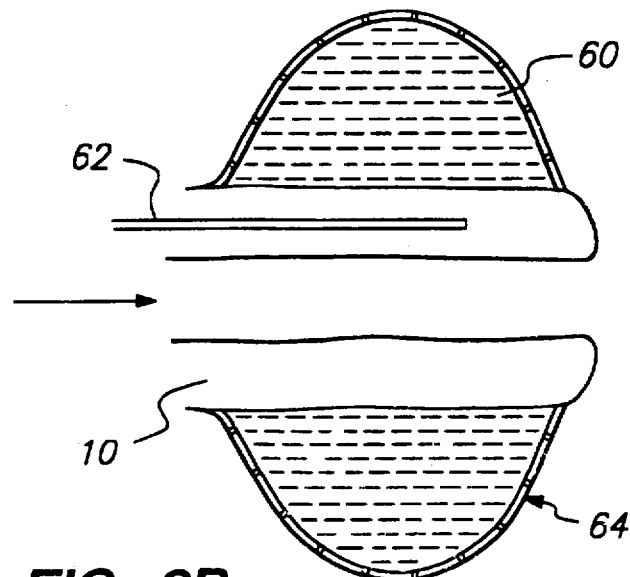
FIG. 6b is a side sectional view of the catheter of FIG. 6a with the swellable portion in a swollen state.

According to the embodiment shown in FIGS. 6a and 6b, a light sensitive material such as a N-isopropylacrylamide-chlorophyllin gel, is formed in the shape of a ring 60 around a catheter 10. In the embodiment shown, the material has been exposed to water and thus is in a swollen gel state. The application of light to the light sensitive gel will cause a phase change and reduction in the volume of the gel. As shown in FIG. 6a, a fiber optic light guide 62 transmits light to the ring of light sensitive gel 60. Light emitted from a light source is applied to an exterior end of the light guide 62. The light transmitted through the light guide 62 causes the gel ring 60 to undergo a phase change and reduce in volume for insertion or removal of the catheter 10. Once the catheter has been inserted, the light source is removed from the light guide 62 and the gel undergoes a reverse phase change and reverts to the swollen configuration shown in FIG. 6b.

Although this embodiment of the invention has been described as employing a separate fiber optic light guide 62, the catheter body 10 itself may also be used as a light guide, when made from a light transmitting material. As shown in FIGS. 6a and 6b, the gel ring 60 is preferably surrounded by a porous protective layer elastomeric layer 64. The protective layer 64 allows urine to pass through the protective layer into the gel as the gel swells, and to pass out of the gel when the gel shrinks upon application of a light source.

Other known stimuli sensitive materials which are suitable for use in the present invention include electrically sensitive materials. For example, one electrically sensitive material which undergoes a rapid electrically induced phase change is cross-linked sodium salt of polyacrylic acid. Numerous other systems are known, and would be applicable to the present invention, such as systems incorporating materials which are sensitive to pH, temperature, or a solvent. However, pH and temperature sensitive materials are somewhat less desirable than light and electrically sensitive materials because the body is subject to temperature and pH changes which may affect such a material. Other methods of activation of the swellable material will be apparent to those skilled in the art.

The response times of stimuli sensitive materials are largely dependent on the rate at which water can enter or exude from the material. Response times can be reduced by employing open cell foam structures, or bundles of micro tubes or fibers, which are contained in a suitable porous elastic casing. Light, heat, or electrical stimulation offer the most readily controllable stimuli for utilization in the devices of the present invention. For temperature based phase changes, small, resistive heaters, such as vapor deposited resistive heaters, can be used, in connection with an external power source.

In yet a further embodiment of the device, the valve of the valved catheter mentioned above with respect to the embodiments of FIGS. 1-4 can be replaced by a stimuli sensitive valve, e.g., a light stimulated sphincter of gel forming material, situated within the lumen of the device. Light can be delivered to such a sphincter via embedded fiber optics or by the catheter itself wherever it is desired to shrink the gel forming material. The retention mechanism or retention head in the catheters and plugs discussed above can also be replaced with a swellable retention head of gel forming material.

While the invention has been described in detail with reference to a preferred embodiment thereof, it will be apparent to one skilled in the art that various changes can be made, and equivalents employed without departing from the spirit and scope of the invention.

What is claimed is:

1. A female incontinence device comprising:
    a body having an enlarged retention head at a first end and a removal or meatal anchor portion at a second end; and
    at least one water swellable ring of a gel forming material disposed about the body for preventing leakage between the body and walls of the urethra.

2. The female incontinence device according to claim 1, wherein the gel forming material swells when it comes into contact with urine.

3. The female incontinence device according to claim 2, wherein the gel forming material is a hydrophilic polymer.

4. The female incontinence device according to claim 1, wherein the gel forming material swells to a predetermined size small enough to allow the device to be removed without causing trauma to the urethra.

5. The female incontinence device according to claim 1, comprising a plurality of rings of the gel forming material, the rings being spaced apart and providing a seal between the body and the walls of the urethra when the rings are in a swollen state.

6. The female incontinence device according to claim 1, wherein the ring is the retention head.

7. The female incontinence device according to claim 1, wherein the ring comprises a conical ring which increases in diameter in a direction away from said first end.

8. The female incontinence device according to claim 1, wherein the ring is formed of a stimuli sensitive polymer which undergoes a phase change and changes size in response to a stimuli.

9. The female incontinence device according to claim 8, wherein the stimuli is selected from the group consisting of light, pH, electrical field, mechanical stress, temperature, and solvent interaction.

10. The female incontinence device according to claim 1, wherein the retention head includes at least one opening and the body is a tubular catheter having a valve which prevents fluid from passing from the retention head, through a lumen of the catheter and outwardly of the removal or meatal anchor portion.

11. The female incontinence device according to claim 1, wherein the body is a sealing plug which prevents passage of urine and is removable to allow a flow of urine.

12. The female incontinence device according to claim 1, wherein the enlarged retention head is expandable to retain the device in the urethra.

13. A female incontinence device comprising:
    a tubular catheter body having an enlarged retention head at a first end thereof and a valve which is actuatable to allow urine to pass from a bladder through the tubular catheter body; and
    at least one water swellable ring of a gel forming material disposed about the tabular catheter body for sealing the catheter body within a female urethra.

14. The female incontinence device according to claim 13, wherein the gel forming material is a water swellable hydrophilic polymer which swells when it comes into contact with urine.

15. The female incontinence device according to claim 13, comprising a plurality of rings of the gel forming material, the rings being spaced apart and providing a seal between the body and the walls of the urethra when the rings are in a swollen state.

16. The female incontinence device according to claim 13, wherein the ring has a conical shape in a swollen state.

17. The female incontinence device according to claim 13, wherein the ring is formed of a stimuli sensitive polymer which undergoes a phase change and changes size in response to a stimuli.

18. The female incontinence device according to claim 17, wherein the stimuli is selected from the group consisting of light, pH, electrical field, mechanical stress, temperature, and solvent interaction.

19. A female incontinence catheter comprising:
    a tubular catheter body having an enlarged retention head at a first end thereof; and
    a water swellable valve of a gel forming material positioned within the catheter which prevents fluid from passing through the tubular catheter body, the gel forming material being of a stimuli sensitive polymer which undergoes a phase change and reduces size in response to a stimuli.

20. The female incontinence catheter according to claim 19, wherein the stimuli is selected from the group consisting of light, pH, electrical field, mechanical stress, temperature, and solvent interaction.

21. The female incontinence catheter according to claim 19, further comprising at least one water swellable ring of a gel forming material disposed about the body for preventing leakage between the body and walls of the urethra.

22. The female incontinence catheter according to claim 19, wherein the gel forming material is a water swellable hydrophilic polymer which swells when it comes into contact with urine.

23. The female incontinence catheter according to claim 22, further comprising a plurality of rings of the gel forming material, the rings being spaced apart and providing a seal between the body and the walls of the urethra when the rings are in a swollen state.

* * * * *